United States Patent
Tan et al.

(10) Patent No.: US 11,201,030 B2
(45) Date of Patent: Dec. 14, 2021

(54) DISTRIBUTED X-RAY LIGHT SOURCE AND CONTROL METHOD THEREFOR, AND CT EQUIPMENT

(71) Applicants: Nuctech Company Limited, Beijing (CN); TSINGHUA UNIVERSITY, Beijing (CN)

(72) Inventors: Chengjun Tan, Beijing (CN); Wenhui Huang, Beijing (CN); Chuanxiang Tang, Beijing (CN); Qingxiu Jin, Beijing (CN); Dongsheng Zhang, Beijing (CN); Qun Luo, Beijing (CN); Donghai Liu, Beijing (CN); Luming Zhang, Beijing (CN); Peidong Wu, Beijing (CN)

(73) Assignees: Nuctech Company Limited, Beijing (CN); TSINGHUA UNIVERSITY, Beijing (CN)

( * ) Notice: Subject to any disclaimer, the term of this patent is extended or adjusted under 35 U.S.C. 154(b) by 0 days.

(21) Appl. No.: 16/627,515

(22) PCT Filed: May 29, 2018

(86) PCT No.: PCT/CN2018/088833
§ 371 (c)(1),
(2) Date: Dec. 30, 2019

(87) PCT Pub. No.: WO2019/052224
PCT Pub. Date: Mar. 21, 2019

(65) Prior Publication Data
US 2020/0170097 A1    May 28, 2020

(30) Foreign Application Priority Data
Sep. 18, 2017 (CN) .......................... 201710842665.0

(51) Int. Cl.
*H01J 35/14* (2006.01)
*G01N 23/046* (2018.01)
(Continued)

(52) U.S. Cl.
CPC ............ *H01J 35/147* (2019.05); *A61B 6/032* (2013.01); *A61B 6/4007* (2013.01);
(Continued)

(58) Field of Classification Search
CPC ........... A61B 6/032; A61B 6/035; A61B 6/40; A61B 6/4007; A61B 6/4021;
(Continued)

(56) References Cited

U.S. PATENT DOCUMENTS

| 5,497,053 A | 3/1996 | Tang et al. |
| 2006/0002515 A1 | 1/2006 | Huber et al. |

(Continued)

FOREIGN PATENT DOCUMENTS

| CN | 106409639 A | 2/2017 |
| CN | 106531592 A | 3/2017 |

(Continued)

OTHER PUBLICATIONS

International Search Report dated Aug. 13, 2018 issued in PCT/CN2018/088833, together with English translation.
(Continued)

*Primary Examiner* — Chih-Cheng Kao
(74) *Attorney, Agent, or Firm* — Scully Scott Murphy & Presser

(57) ABSTRACT

A distributed X-ray light source comprises: a plurality of arranged cathode assemblies used for emitting electron beams; an anode target used for receiving the electron beams emitted by the cathode assemblies; and compensation electrodes and focusing electrodes provided in sequence between the plurality of the cathode assemblies and the
(Continued)

anode target, the compensation electrode being used for adjusting electric field strength at two ends of a grid structure in each cathode assembly, and the focusing electrode being used for focusing the electron beams emitted by the cathode assemblies, wherein the focusing electrode corresponding to at least one cathode assembly in the plurality of the cathode assemblies comprises a first electrode and a second electrode which are separately provided, and an electron beam channel is formed between the first electrode and the second electrode.

9 Claims, 3 Drawing Sheets

(51) Int. Cl.
| | | |
|---|---|---|
| *A61B 6/03* | (2006.01) | |
| *H01J 35/04* | (2006.01) | |
| *A61B 6/00* | (2006.01) | |
| *H05G 1/52* | (2006.01) | |
| *H05G 1/32* | (2006.01) | |

(52) U.S. Cl.
CPC .......... *G01N 23/046* (2013.01); *H01J 35/045* (2013.01); *H05G 1/52* (2013.01); *A61B 6/035* (2013.01); *H05G 1/32* (2013.01)

(58) Field of Classification Search
CPC ... G01N 23/046; G01N 23/043; H01J 35/045; H01J 35/147; H01J 35/06; H01J 35/14; H01J 35/153; H01J 35/30; H05G 1/32; H05G 1/70; H05G 1/52
See application file for complete search history.

(56) References Cited

U.S. PATENT DOCUMENTS

| | | | |
|---|---|---|---|
| 2009/0022264 A1 | 1/2009 | Zhou et al. | |
| 2014/0219424 A1* | 8/2014 | Smith | H05G 1/52 378/137 |
| 2015/0110252 A1* | 4/2015 | Yun | G21K 1/06 378/138 |
| 2015/0124934 A1* | 5/2015 | Gupta | H01J 35/065 378/122 |
| 2017/0248532 A1* | 8/2017 | Kadambi | G01N 23/046 |
| 2017/0263413 A1* | 9/2017 | Frosien | H01J 37/12 |

FOREIGN PATENT DOCUMENTS

| | | |
|---|---|---|
| CN | 107464734 A | 12/2017 |
| CN | 207165514 U | 3/2018 |
| DE | 4425683 A1 | 1/1996 |

OTHER PUBLICATIONS

Partial Supplementary European Search Report dated May 11, 2021 received in European Patent Application No. EP 18855412.5.
Extended European Search Report dated Sep. 24, 2021 received in European Patent Application No. EP 18855412.5.

* cited by examiner

DISTRIBUTED X-RAY LIGHT SOURCE AND CONTROL METHOD THEREFOR, AND CT EQUIPMENT

CROSS-REFERENCE

The present disclosure is the 371 application of PCT Application No. PCT/CN2018/088833, filed on May 29, 2018, which is based upon and claims the priority to the Chinese Patent Application NO. 201710842665.0, entitled "DISTRIBUTED X-RAY LIGHT SOURCE AND CONTROL METHOD THEREFOR, AND CT EQUIPMENT", filed on Sep. 18, 2017, the entire contents of which are hereby incorporated by reference.

TECHNICAL FIELD

The present disclosure relates to the field of X-ray technologies, and in particular to a distributed X-ray light source, a control method thereof and a CT device.

BACKGROUND

X-rays have a wide range of applications in industrial non-destructive testing, safety inspection, medical diagnosis and treatment, and so on. In particular, X-ray fluoroscopic imaging devices utilizing high penetrating capability of K-rays play an important role in every aspect of people's daily life. In the early days, such devices are film-type planar fluoroscopy imaging devices. At present, they have developed into digital, multi-view and high-resolution stereo imaging devices, such as Computed Tomography (CT) imaging device, which can obtain three-dimensional graphics or slice images of high-definition.

FIG. 1 is a schematic structural diagram of a distributed X-ray light source in the related art. The distributed X-ray light source includes a plurality of cathode assemblies (101A, 101B, 101C, ..., 101N), a compensation electrode 103, a focusing electrode 104, an anode target 102, a power supply system (such as a high voltage power supply and a compensation and focusing power supply shown in FIG. 1) and the like. In the structure shown in FIG. 1, by referring to FIG. 2, electron beams emitted from a cathode 1011 in the cathode assembly pass through the compensation electrode 103 and the focusing electrode 104, and bombard only one target spot on the anode target 102, and then an X-ray radiation source is generated. Affected by the size of the cathode and the processing of the cathode assembly, currently the minimum diameter of the cathode assembly is about 16 mm, and leaving a small margin, the cathode assemblies are usually arranged at a spacing of 20 mm. In a light source with a length of 1 (one) meter, 50 cathode assemblies can be arranged. One cathode assembly produces a target spot on the anode target, thereby forming 50X-ray radiation sources.

As the cathode in the cathode assembly, a thermionic dispenser cathode, a working temperature of which is about 1100° C., is usually used. A heating power of a single cathode is about 8 W, then 50 cathodes have the heating power of about 400 W. Such a high heating power will cause a very high temperature of a holder of the cathode assembly. According to the current experimental results, at the positions where the holder made of the stainless steel and the cathode assembly are crimped, the temperature is up to 300° C., which makes the thermal management of the cathode assembly extremely difficult, and an additional cooling device is required to cool the cathode assembly, or a material with better thermal conductivity is required to be processed as the holder of the cathode assembly, which increases the production cost of the device.

It should be noted that the information disclosed in the Background section above is only for enhancing the understanding of the background of the present disclosure, and thus may include information that does not constitute prior art known to those of ordinary skill in the art.

SUMMARY

An object of the present disclosure is to provide a distributed X-ray light source, a control method therefor and a CT device.

Other features and advantages of the present disclosure will be apparent from the following detailed description, or learned in part by the practice of the present disclosure.

According to a first aspect of embodiments of the present disclosure, there is provided a distributed X-ray light source including: a plurality of arranged cathode assemblies, configured to emit electron beams; an anode target, configured to receive the electron beams emitted by the cathode assemblies; and compensation electrodes and focusing electrodes provided in sequence between the plurality of the cathode assemblies and the anode target, the compensation electrodes being configured to adjust electric field strength between two ends of a grid structure in each cathode assembly, the focusing electrodes being configured to focus the electron beams emitted by the cathode assemblies, wherein the focusing electrode corresponding to at least one cathode assembly in the plurality of the cathode assemblies includes a first electrode and a second electrode which are separately provided, and an electron beam channel is formed between the first electrode and the second electrode.

In some embodiments of the present disclosure, the focusing electrode corresponding to each of the at least one cathode assembly is disposed separately.

In some embodiments of the present disclosure, the first electrodes corresponding to all of the at least one cathode assembly are electrically connected to each other and connected to a first power source, and the second electrodes corresponding to all of the at least one cathode assembly are electrically connected to each other and connected to a second power source, and voltages of the first power source and the second power source are adjustable.

In some embodiments of the present disclosure, two focusing electrodes corresponding to any two adjacent cathode assemblies of the at least one cathode assembly have a common electrode, and the common electrode serves as a second electrode of a first focusing electrode in the two focusing electrodes and a first electrode of a second focusing electrode in the two focusing electrodes.

In some embodiments of the present disclosure, the first electrode corresponding to a first cathode assembly in an arrangement order of the at least one cathode assembly and the second electrode corresponding to the cathode assemblies arranged in even numbers in the arrangement order are electrically connected to each other and connected to a first power source; and the second electrodes corresponding to the cathode assemblies arranged in odd numbers in the arrangement order of the at least one cathode assembly are electrically connected to each other and connected to a second power source, and voltages of the first power source and the second power source are adjustable.

In some embodiments of the present disclosure, the distributed X-ray light source further includes: a voltage control module, connected to the first power source and the second power source and configured to control the voltages of the first power source and the second power source so as to adjust a voltage difference between the first power source and the second power source.

In some embodiments of the present disclosure, each of the focusing electrodes corresponding to all of the plurality of cathode assemblies includes the first electrode and the second electrode which are provided separately.

In some embodiments of the present disclosure, each cathode assembly includes: a cathode, configured to emit the electron beams; and the grid structure, disposed in a direction of an emitting end of the cathode and spaced from the emitting end of the cathode at a predetermined distance.

According to a second aspect of the embodiments of the present disclosure, there is provided a CT device including the distributed X-ray light source of any of the above embodiments.

According to a third aspect of the present disclosure, a method for controlling a distributed X-ray light source is provided to control the distributed X-ray light source of any of the above embodiments, the control method including: sequentially adjusting a voltage difference between the first electrode and the second electrode corresponding to each of at least one cathode assembly according to a predetermined cycle so as to control positions at which electron beams emitted by each of the at least one cathode assembly bombard the anode target.

It should be noted that the above general description and the following detailed description are merely exemplary and explanatory and should not be construed as limiting of the disclosure.

BRIEF DESCRIPTION OF THE DRAWINGS

The accompanying drawings, which are incorporated in the specification and constitute a part of the specification, show exemplary embodiments of the present disclosure. The drawings along with the specification explain the principles of the present disclosure. It is apparent that the drawings described below show only some embodiments of the present disclosure, and other drawings can be obtained by those skilled in the art from the drawings described herein without creative effort.

DETAILED DESCRIPTION

Exemplary embodiments will now be described more comprehensively with reference to the accompanying drawings. However, the exemplary embodiments can be implemented in a variety of forms and should not be construed as being limited to the embodiments set forth herein; rather, these embodiments are provided so that this disclosure will be more complete and the idea of the exemplary embodiments will be completely conveyed to those skilled in this art.

In addition, the described features, structures, or characteristics can be combined in one or more embodiments in any suitable manner. In the following description, numerous specific details are set forth to provide a thorough understanding of the embodiments of the present disclosure. However, one skilled in the art will appreciate that the technical solutions of the present disclosure can be practiced without one or more of the specific details, or can be practiced with other methods, components, materials, devices, steps, or the like. In other instances, well-known methods, devices, implementations or operations are not shown or described in detail so as to avoid obscuring aspects of the present disclosure.

Embodiment 1

Figure 1:
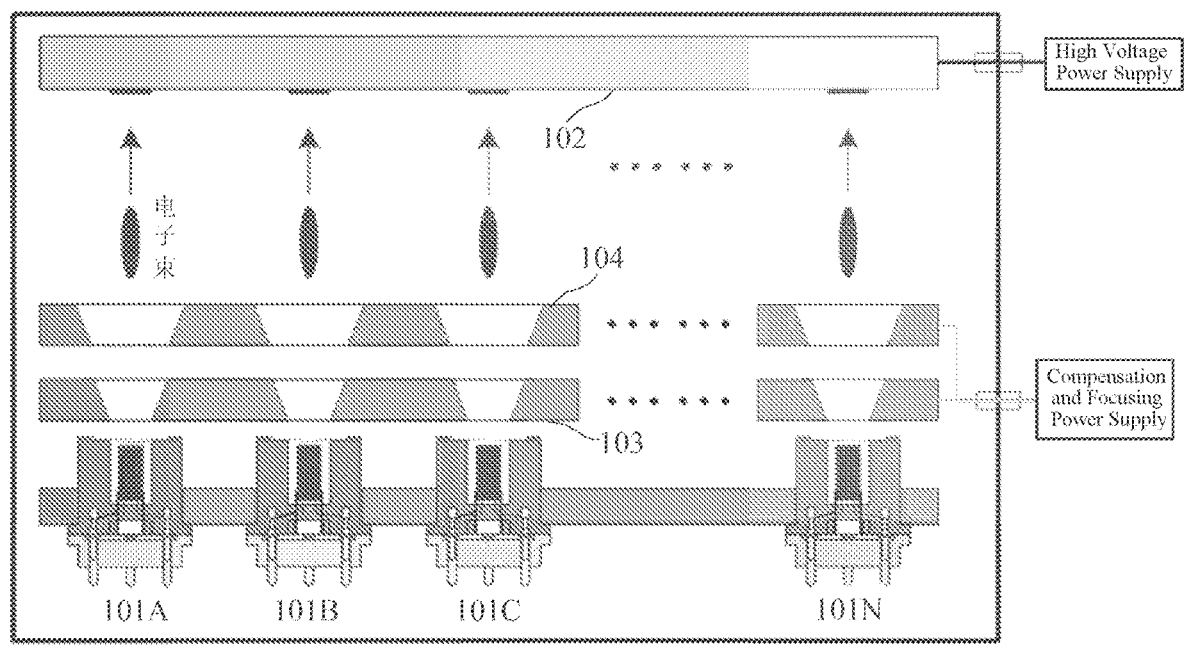
FIG. 1 shows a schematic structural diagram of a distributed X-ray light source in the related art.
Figure 2:
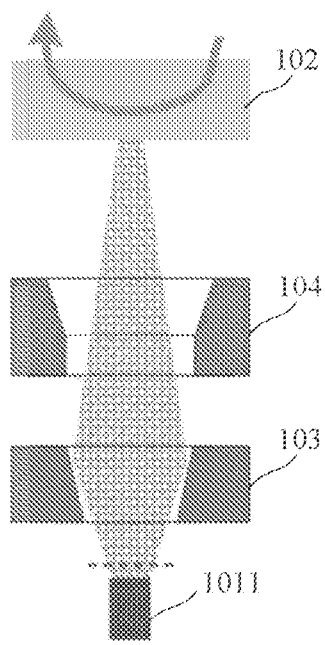
FIG. 2 shows a schematic diagram of a movement trajectory of electron beams emitted by a cathode assembly based on the structure of the distributed X-ray light source shown in FIG. 1.
Figure 3:
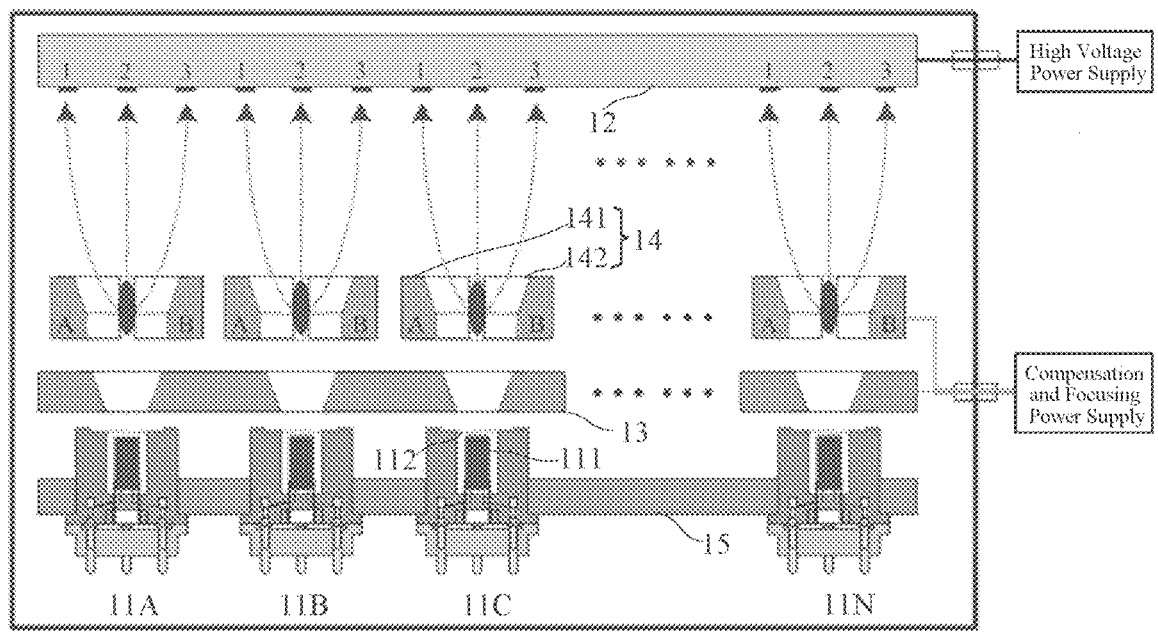
FIG. 3 shows a schematic structural diagram of a distributed X-ray light source according to a first embodiment of the present disclosure.

Referring to FIG. 3, a distributed X-ray light source according to a first embodiment of the present disclosure includes: a plurality of arranged cathode assemblies (such as cathode assemblies 11A, 11B, 11C, . . . , 11N shown in FIG. 3), an anode target 12, and compensation electrodes 13 and focusing electrodes 14 disposed in sequence between the plurality of cathode assemblies and the anode target 12. In an embodiment of the present disclosure, the plurality of cathode assemblies can be disposed in sequence on a mounting and fixing plate 15.

Figure 4:
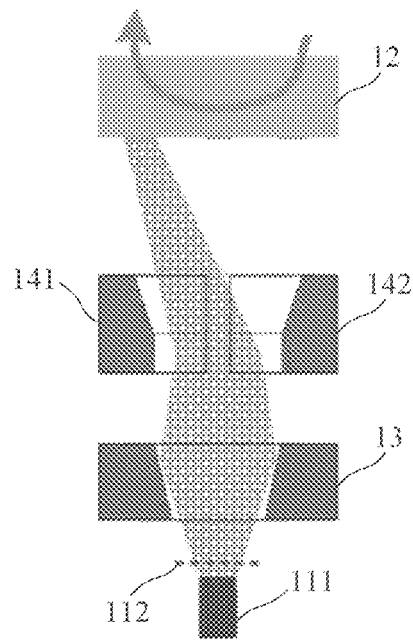
FIG. 4 shows a schematic diagram of a movement trajectory of electron beams emitted by cathode assemblies according to an embodiment of the present disclosure.

The cathode assemblies are configured to emit electron beams. In the embodiment of the present disclosure, as shown in FIGS. 3 and 4, each of the cathode assemblies includes a cathode 111 and a grid structure 112. The cathode 111 is configured to emit the electron beams, and the grid structure 112 is disposed in a direction of an emitting end of the cathode 111, and is spaced from the emitting end of the cathode 111 at a predetermined distance. When the grid structure 112 is at a positive potential, the cathode 111 emits the electron beams, and when the grid structure 112 is at a negative potential, the cathode 111 is turned off and does not emit the electron beams.

The anode target 12 is configured to receive the electron beams emitted by the cathode assemblies and convert energy of the electron beams into the X-ray radiation source while taking excess energy away through a cooling medium. Each of the compensation electrodes 13 is configured to adjust the electric field strength between two ends of the grid structure 112, so that, on the one hand, the electron beams can quickly pass through the grid structure 112, reducing the interception rate of the electron beams on the grid structure 112, and on the other hand, the voltage of each compensation electrode 13 is adjusted so that the electric field strength between the two ends of each grid structure 112 is substantially uniform, thereby avoiding the problem of increased emissivity after the electron beams pass through the grid structure 112, and ensuring that the electron beams focus more easily.

The focusing electrodes 14 are configured to focus the electron beams emitted by the cathode assemblies, thereby ensuring that the focal spots generated by the electron beams bombarding the anode target 12 have suitable sizes. In an embodiment of the present disclosure, as shown in FIG. 3, the focusing electrodes 14 corresponding to at least one of the plurality of cathode assemblies include a first electrode 141 and a second electrode 142 disposed separately. An electron beam channel is formed between the first electrode 141 and the second electrodes 142. It is to be noted that, in the structure shown in FIG. 3, the focusing electrodes 14 corresponding to all of the cathode assemblies each includes the separately disposed first electrode 141 and second electrode 142. In some other embodiments of the present disclosure, in the distributed X-ray light source, there may be only one focusing electrode corresponding to one cathode assembly having the structure shown in FIG. 3, or the focusing electrodes corresponding to some of the plurality of cathode assemblies have the structures shown in FIG. 3.

As shown in FIG. 4, since the focusing electrode 14 is disposed into the first electrode 141 and the second electrode 142, the electron beams can bombard the anode target 12 at different positions by changing the voltage difference between the first electrode 141 and the second electrode 142. For example, when the voltage difference between the first electrode 141 and the second electrode 142 is $+V_{def1}$, the electron beams are not only focused but also shifted toward the direction of the first electrode 141 (as shown in FIG. 4) when passing through the focusing electrode 14. When the voltage difference between the first electrode 141 and the second electrode 142 is $-V_{def1}$, the electron beams are not only focused but also shifted toward the direction of the second electrode 142 when passing through the focusing electrode 14. When the voltage difference between the first electrode 141 and the second electrode 142 is 0, the electron beams are only focused without being shifted when passing through the focusing electrode 14. As such, the electron beams emitted by one cathode assembly can bombard the anode target 12 at different positions, thereby effectively reducing the number of the cathode assemblies used while ensuring a certain number of X-ray radiation sources.

Specifically, if an offset distance of the electron beams is set to 10 mm and the electron beams emitted by one cathode assembly bombard 3 target spots on the anode target, a mounting space of the cathode assemblies is 30 mm, and the number of cathode assemblies that can be mounted in a length of 1 m is 33. 33 cathode assemblies can produce 99 light sources, which achieves the effect of producing more target spots by using fewer cathode assemblies, thereby reducing the production cost of the system, and reducing the thermal management difficulty of the mounting and fixing plates of the cathode assemblies at the same time.

In the embodiment of the present disclosure, as shown in FIG. 3, the focusing electrodes 14 corresponding to the respective cathode assemblies are disposed separately, that is, the focusing electrodes corresponding to the respective cathode assemblies are separated from each other.

In order to control the respective focusing electrodes shown in FIG. 3, in the embodiment of the present disclosure, the first electrodes 141 corresponding to all the cathode assemblies can be connected to each other and then connected to a first power source, and the second electrodes 142 corresponding to all the cathode assemblies can be connected to each other and then connected to a second power source. The voltages of the first power source and the second power source are adjustable. Specifically, the electrical connection can be made by a vacuum cable.

In an embodiment of the present disclosure, a voltage control module can be disposed to connected the first power source and the second power source so as to adjust the voltage difference between the first power source and the second power source by controlling the voltages of the first power source and the second power source.

Specifically, for the distributed X-ray light source shown in FIG. 3, when the first power source and the second power source are controlled by the voltage control module to maintain a voltage difference therebetween, the cathode assemblies can be controlled to emit the electron beams one by one. After all of the cathode assemblies have emitted the electron beams, the first power source and the second power source are controlled to maintain another voltage difference therebetween, and then the cathode assemblies are controlled to emit the electron beams one by one. The scanning process is realized in this cycling manner.

For example, when the voltage difference between the first power source and the second power source is $+V_{def1}$, the electron beams emitted by the individual cathode assemblies will bombard the respective "1" positions on the anode target 12, when the voltage difference between the first power source and the second power source is 0, the electron beams emitted by the individual cathode assemblies will bombard the respective "2" positions on the anode target 12, and when the voltage difference between the first power source and the second power source is $-V_{def1}$, the electron beams emitted by the individual cathode assemblies will bombard the respective "3" positions on the anode target 12.

In addition, by adjusting the voltage difference between the first power source and the second power source, the electron beams can bombard the anode target at any position, thereby realizing that one cathode assembly can produce a plurality of target spots, such as 4, 5, 6, and 7 target spots.

Embodiment 2

Figure 5:
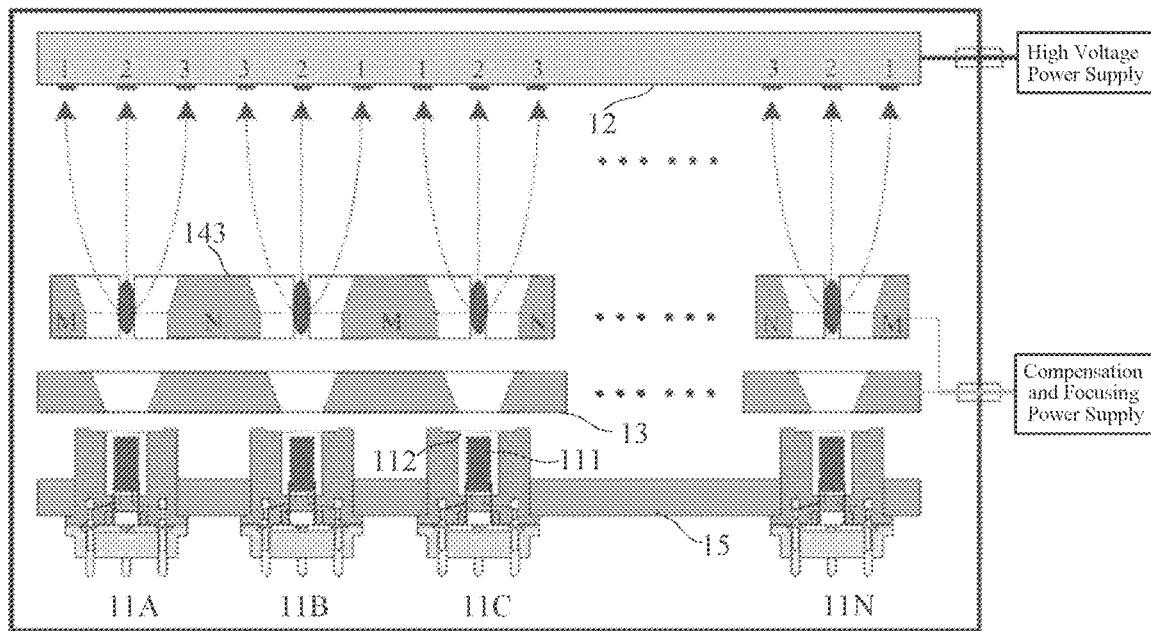
FIG. 5 shows a schematic structural diagram of a distributed X-ray light source according to a second embodiment of the present disclosure.

Referring to FIG. 5, a distributed X-ray light source according to a second embodiment of the present disclosure includes: a plurality of arranged cathode assemblies (such as cathode assemblies 11A, 11B, 11C, . . . , 11N as shown in FIG. 5), an anode target 12, and compensation electrodes 13 and focusing electrodes 14 disposed in sequence between the plurality of cathode assemblies and the anode target 12. In an embodiment of the present disclosure, the plurality of cathode assemblies can be disposed in sequence on the mounting and fixing plate 15.

The functions and the disposing modes of the cathode assemblies, the anode target 12 and the compensation electrodes 13 are similar to those of the first embodiment, and will not be described herein again.

Similarly, in the second embodiment, similarly to the first embodiment, the focusing electrode corresponding to each cathode assembly is divided into the first electrode and the second electrode which are disposed separately. An electron beam channel is formed between the two electrodes. Referring to FIG. 5, differently from the first embodiment, two focusing electrodes corresponding to any two adjacent cathode assemblies have a common electrode, which is used as the second electrode of a first focusing electrode and the first electrode of a second focusing electrode in the two focusing electrodes. Specifically, as shown in FIG. 5, the focusing electrode corresponding to the cathode assembly 11A and the focusing electrode corresponding to the cathode assembly 11B have a common electrode 143, which is used as the second electrode of the cathode assembly 11A and the first electrode of the cathode assembly 11B.

It should also be noted that, in the structure shown in FIG. 5, the focusing electrodes corresponding to all the cathode assemblies include the first electrode and the second electrode disposed separately. In some other embodiments of the present disclosure, in the distributed X-ray light sources, only a part of the focusing electrodes corresponding to the cathode assemblies may have the structure shown in FIG. 5

In the embodiment of the present disclosure, for the structure shown in FIG. 5, according to the arrangement order of the plurality of cathode assemblies, the first electrode corresponding to the first cathode assembly and the second electrodes corresponding to the cathode assemblies arranged in even numbers in the arrangement order can be connected to each other and then connected to the first power source, and the second electrodes corresponding to the cathode assemblies arranged in odd numbers in the arrangement order can be connected to each other and then connected to the second power source. Specifically, for the structure shown in FIG. 5, the first electrode corresponding to the cathode assembly 11A (the first cathode assembly) and the second electrode corresponding to the cathode assembly 11B (of arrangement number 2) and so on can be electrically connected to each other and then connected to the first power source, the second electrode corresponding to the cathode electrode 11A (of arrangement number 1) and the second electrode corresponding to the cathode assembly 11C (of arrangement number 3) and so on are electrically connected to each other and then connected to the second power source. Specifically, the electrical connection can be made through a vacuum cable. Compared with the structure shown in FIG. 3, the structure shown in FIG. 5 can reduce the number of connections of the vacuum cables.

Similar to the first embodiment, the voltage control module can be disposed to connect the first power source and the second power source so as to adjust the voltage difference between the first power source and the second power source by controlling the voltages of the first power source and the second power source.

Specifically, for the distributed X-ray light source shown in FIG. 5, when the first power source and the second power source are controlled by the voltage control module to maintain a voltage difference therebetween, the cathode assemblies can be controlled to emit the electron beams one by one. After all of the cathode assemblies have emitted the electron beams, the first power source and the second power source are controlled to maintain another voltage difference therebetween, and then the cathode assemblies are controlled to emit the electron beams one by one. The scanning process is realized in this cycling manner.

For example, when the voltage difference between the first power source and the second power source is $+V_{defl}$, the electron beams emitted by the individual cathode assemblies will bombard the respective "1" positions on the anode target 12, when the voltage difference between the first power source and the second power source is 0, the electron beams emitted by the individual cathode assemblies will bombard the respective "2" positions on the anode target 12, and when the voltage difference between the first power source and the second power source is $-V_{defl}$, the electron beams emitted by the individual cathode assemblies will bombard the respective "3" positions on the anode target 12. It should be noted that since the connection manner of the focusing electrodes corresponding to the respective cathode assemblies in the structure shown in FIG. 5 to the first power source or the second power source is different from that of the first embodiment, the scanning order in which the adjacent cathode assemblies in FIG. 5 emit the electron beams is reversed.

Figure 6:
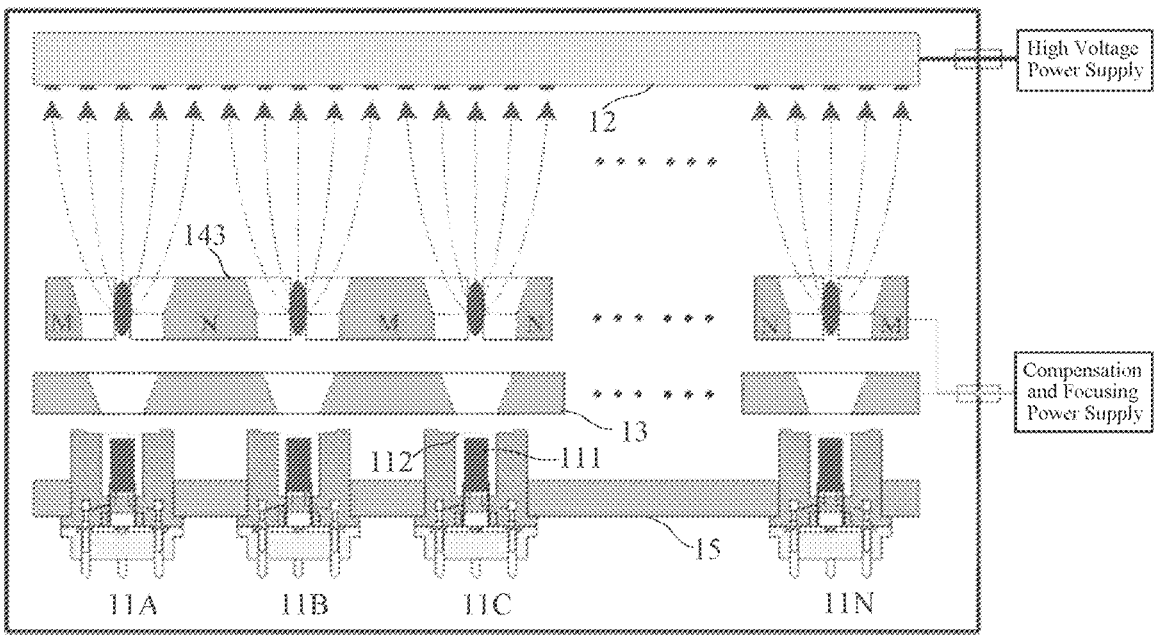
FIG. 6 shows a schematic diagram of bombarding five target spots on an anode target based on a structure of the distributed X-ray light source shown in FIG. 5.

In addition, by adjusting the voltage difference between the first power source and the second power source, the electron beams can bombard the anode target at any position, thereby realizing that one cathode assembly can produce a plurality of target spots, such as 4, 5, 6, and 7 target spots. Specifically, as shown in FIG. 6, by controlling the voltage difference between the first power source and the second power source, one cathode component can produce five target spots.

In addition, for the distributed X-ray light source in the above embodiment, the embodiments of the present disclosure also provides a method for controlling a distributed X-ray light source, which includes: sequentially adjusting a voltage difference between a first electrode and a second electrode corresponding to each of the at least one cathode assembly according to a predetermined cycle so as to control positions at which the electron beams emitted by each of the at least one cathode assembly bombard the anode target, which achieves the effect of producing more target spots by using fewer cathode assemblies, reducing the number of the cathode assemblies used in the distributed X-ray light source, reducing the temperature of the holder of the cathode assemblies and the thermal management difficulty, improving the stability of the system and reducing the production cost of the device.

In the technical solutions provided by some embodiments of the present disclosure, the focusing electrode corresponding to the cathode assembly is disposed into the separated first electrode and second electrode, and the electron beam channel is formed between the first electrode and the second electrode, so that the electron beams emitted by the cathode assembly are shifted by the voltage difference between the first electrode and the second electrode when passing through the focusing electrode, and thus the positions at which the electron beams bombard the anode target can be controlled by controlling the voltage difference between the first electrode and the second electrode, and the electron beams emitted by one cathode assembly can be controlled to bombard the anode target at different positions, which achieves the effect of producing more target spots by using fewer cathode assemblies, reducing the number of the cathode assemblies used in the distributed X-ray light source, reducing the temperature of the holder of the cathode assemblies and the thermal management difficulty, improving the stability of the system and reducing the production cost of the device.

It should be noted that although modules or units of devices for executing functions are referred to in the above descriptions, such division of modules or units is not mandatory. In fact, features and functions of two or more of the modules or units described above may be embodied in one module or unit in accordance with the embodiments of the present disclosure. Conversely, the features and functions of one module or unit described above may be further divided into multiple modules or units.

Other embodiments of the present disclosure will be apparent to those skilled in the art in consideration of the description and in the practice of the present disclosure. The present disclosure is intended to cover any variations, uses, or adaptations of the present disclosure, which are made in accordance with the general principles of the present disclosure and include common knowledge or conventional technical means in the art that are not disclosed in the present disclosure. The specification and embodiments are illustrative, and the real scope and spirit of the present disclosure are indicated by the appended claims.

It should be understood that the present disclosure is not limited to the precise structures that have been described above and shown in the drawings, and various modifications and changes can be made without departing from the scope thereof. The scope of the present disclosure is only limited by the appended claims.

What is claimed is:

1. A distributed X-ray light source, comprising:
a plurality of arranged cathode assemblies, configured to emit electron beams;
an anode target, configured to receive the electron beams emitted by the cathode assemblies; and
compensation electrodes and focusing electrodes provided in sequence between the plurality of the cathode assemblies and the anode target, the compensation electrodes being configured to adjust electric field strength between two ends of a grid structure in each cathode assembly, and the focusing electrodes being configured to focus the electron beams emitted by the cathode assemblies;
wherein the focusing electrode corresponding to at least one cathode assembly in the plurality of the cathode assemblies includes a first electrode and a second electrode which are provided separately, and an electron beam channel is formed between the first electrode and the second electrode,
wherein:
the focusing electrode corresponding to each of the at least one cathode assembly is disposed separately; the focusing electrodes corresponding to at least two cathode assemblies of the plurality of the cathode assemblies each include the first electrode and the second electrode; the first electrodes are electrically connected to each other and connected to a first power source, and the second electrodes are electrically connected to each other and connected to a second power source; and voltages of the first power source and the second power source are adjustable; or
the at least one cathode assembly comprises two adjacent cathode assemblies, and two focusing electrodes corresponding to the two adjacent cathode assemblies have a common electrode; the common electrode serves as a second electrode of a first focusing electrode in the two focusing electrodes and a first electrode of a second focusing electrode in the two focusing electrodes; the first electrode corresponding to a first cathode assembly in an arrangement order of the at least one cathode assembly and the second electrode corresponding to the cathode assemblies arranged in even numbers in the arrangement order are electrically connected to each other and connected to a first power source; the second electrodes corresponding to the cathode assemblies arranged in odd numbers in the arrangement order of the at least one cathode assembly are electrically connected to each other and connected to a second power source; and voltages of the first power source and the second power source are adjustable.

2. The distributed X-ray light source according to claim 1, further comprising:
a voltage control module, connected to the first power source and the second power source and configured to control the voltages of the first power source and the second power source so as to adjust a voltage difference between the first power source and the second power source.

3. The distributed X-ray light source according to claim 1, wherein each of the focusing electrodes corresponding to all of the plurality of cathode assemblies comprises the first electrode and the second electrode which are provided separately.

4. The distributed X-ray light source according to claim 1, wherein each of the plurality of cathode assemblies comprises:
a cathode, configured to emit the electron beams; and
the grid structure disposed in a direction of an emitting end of the cathode and spaced from the emitting end of the cathode at a predetermined distance.

5. A Computed Tomography (CT) device, comprising: a distributed X-ray light source, the distributed X-ray light source comprising:
a plurality of arranged cathode assemblies, configured to emit electron beams;
an anode target, configured to receive the electron beams emitted by the cathode assemblies; and
compensation electrodes and focusing electrodes provided in sequence between the plurality of the cathode assemblies and the anode target, the compensation electrodes being configured to adjust electric field strength between two ends of a grid structure in each cathode assembly, and the focusing electrodes being configured to focus the electron beams emitted by the cathode assemblies;
wherein the focusing electrode corresponding to at least one cathode assembly in the plurality of the cathode assemblies includes a first electrode and a second electrode which are provided separately, and an electron beam channel is formed between the first electrode and the second electrode,
wherein:
the focusing electrode corresponding to each of the at least one cathode assembly is disposed separately; the focusing electrodes corresponding to at least two cathode assemblies of the plurality of the cathode assemblies each include the first electrode and the second electrode; the first electrodes are electrically connected to each other and connected to a first power source, and the second electrodes are electrically connected to each other and connected to a second power source; and voltages of the first power source and the second power source are adjustable; or
the at least one cathode assembly comprises two adjacent cathode assemblies, and two focusing electrodes corresponding to the two adjacent cathode assemblies have a common electrode; the common electrode serves as a second electrode of a first focusing electrode in the two focusing electrodes and a first electrode of a second focusing electrode in the two focusing electrodes; the first electrode corresponding to a first cathode assembly in an arrangement order of the at least one cathode assembly and the second electrode corresponding to the cathode assemblies arranged in even numbers in the arrangement order are electrically connected to each other and connected to a first power source; the second electrodes corresponding to the cathode assemblies arranged in odd numbers in the arrangement order of the at least one cathode assembly are electrically connected to each other and connected to a second power source; and voltages of the first power source and the second power source are adjustable.

6. The CT device according to claim 5, wherein the distributed X-ray light source further comprises:
a voltage control module, connected to the first power source and the second power source and configured to control the voltages of the first power source and the second power source so as to adjust a voltage difference between the first power source and the second power source.

7. The CT device according to claim 5, wherein each of the focusing electrodes corresponding to all of the plurality of cathode assemblies comprises the first electrode and the second electrode which are provided separately.

8. The CT device according to claim 5, wherein each of the plurality of cathode assemblies comprises:
a cathode, configured to emit the electron beams; and
the grid structure disposed in a direction of an emitting end of the cathode and spaced from the emitting end of the cathode at a predetermined distance.

9. A method for controlling a distributed X-ray light source, the distributed X-ray light source comprising a plurality of arranged cathode assemblies, configured to emit electron beams; an anode target, configured to receive the electron beams emitted by the cathode assemblies; and compensation electrodes and focusing electrodes provided in sequence between the plurality of the cathode assemblies and the anode target, the compensation electrodes being configured to adjust electric field strength between two ends of a grid structure in each cathode assembly, and the focusing electrodes being configured to focus the electron beams emitted by the cathode assemblies, the focusing electrode corresponding to at least one cathode assembly in the plurality of the cathode assemblies including a first electrode and a second electrode which are provided separately, and an electron beam channel being formed between the first electrode and the second electrode, the method comprising:
sequentially adjusting a voltage difference between the first electrode and the second electrode corresponding to each of the at least one cathode assembly according to a predetermined cycle so as to control positions at which the electron beams emitted by each of the at least one cathode assembly bombard the anode target,
wherein:
the focusing electrode corresponding to each of the at least one cathode assembly is disposed separately; the first electrodes corresponding to all of the at least one cathode assembly are electrically connected to each other and connected to a first power source, and the second electrodes corresponding to all of the at least one cathode assembly are electrically connected to each other and connected to a second power source; and voltages of the first power source and the second power source are adjustable, or
the at least one cathode assembly comprises two adjacent cathode assemblies, and two focusing electrodes corresponding to the two adjacent cathode assemblies have a common electrode; the common electrode serves as a second electrode of a first focusing electrode in the two focusing electrodes and a first electrode of a second focusing electrode in the two focusing electrodes; the first electrode corresponding to a first cathode assembly in an arrangement order of the at least one cathode assembly and the second electrode corresponding to the cathode assemblies arranged in even numbers in the arrangement order are electrically connected to each other and connected to a first power source; the second electrodes corresponding to the cathode assemblies arranged in odd numbers in the arrangement order of the at least one cathode assembly are electrically connected to each other and connected to a second power source; and voltages of the first power source and the second power source are adjustable.

* * * * *